(12) United States Patent
Blanchard et al.

(10) Patent No.: US 9,887,425 B2
(45) Date of Patent: Feb. 6, 2018

(54) PRINTED BATTERY ARRAY OUTPUTTING SELECTABLE VOLTAGE AND CURRENT

(71) Applicant: Printed Energy Pty. Ltd., Brisbane, Queensland (AU)

(72) Inventors: Richard Austin Blanchard, Los Altos, CA (US); William Johnstone Ray, Fountain Hills, AZ (US); Mark David Lowenthal, Vancouver, WA (US); Thomas Frederick Soules, Livermore, CA (US); Vera Lockett, Phoenix, AZ (US)

(73) Assignee: Printed Energy Pty. Ltd., Brisbane (AU)

( * ) Notice: Subject to any disclaimer, the term of this patent is extended or adjusted under 35 U.S.C. 154(b) by 220 days.

(21) Appl. No.: 14/994,030

(22) Filed: Jan. 12, 2016

(65) Prior Publication Data

US 2016/0218373 A1 Jul. 28, 2016

Related U.S. Application Data

(60) Provisional application No. 62/108,888, filed on Jan. 28, 2015.

(51) Int. Cl.
| | |
|---|---|
| *H02J 7/00* | (2006.01) |
| *H01M 6/50* | (2006.01) |
| *H01M 6/40* | (2006.01) |
| *A61B 5/00* | (2006.01) |
| *H01M 10/42* | (2006.01) |
| *H01M 10/48* | (2006.01) |

(52) U.S. Cl.
CPC ......... *H01M 6/5011* (2013.01); *A61B 5/6833* (2013.01); *H01M 6/40* (2013.01); *H01M 10/425* (2013.01); *H01M 10/48* (2013.01); *H02J 7/0024* (2013.01); *H02J 7/0063* (2013.01); *H01M 2010/4271* (2013.01); *H01M 2220/30* (2013.01); *H02J 2007/0067* (2013.01)

(58) Field of Classification Search
CPC .............................. H01M 6/40; H01M 6/5011
USPC .................................................. 320/116–123
See application file for complete search history.

(56) References Cited

U.S. PATENT DOCUMENTS

| | | | | |
|---|---|---|---|---|
| 7,898,223 B2 * | 3/2011 | Takeda | ..................... | H02M 3/07 320/117 |
| 2003/0071523 A1 * | 4/2003 | Silverman | ............... | H01M 2/20 307/150 |

\* cited by examiner

*Primary Examiner* — Drew A Dunn
*Assistant Examiner* — Zixuan Zhou
(74) *Attorney, Agent, or Firm* — Patent Law Group LLP; Brian D. Ogonowsky

(57) ABSTRACT

A plurality of batteries is printed on a flexible substrate, where each battery may output the same voltage, such as about 1.5 volts. Batteries in a first subset are connectable in parallel by controllable switches to control the maximum current that can be delivered to a load. Batteries in a second subset are also connectable in parallel by additional controllable switches to control the maximum current that can be delivered to the load. Another group of switches can either connect the two subsets of batteries in series, to generate 3 volts, or connect the subsets in parallel to increase the maximum current. Additional subsets of batteries and their associated switches may be further connected to increase the voltage and current. The power supply may be standardized and configured by the user for a particular load, such as a sensor for a medical skin patch.

20 Claims, 2 Drawing Sheets

PRINTED BATTERY ARRAY OUTPUTTING SELECTABLE VOLTAGE AND CURRENT

CROSS-REFERENCE TO RELATED APPLICATIONS

This application is based on U.S. provisional application Ser. No. 62/108,888, filed Jan. 28, 2015, by Richard Austin Blanchard et al., assigned to the present assignee and incorporated herein by reference.

FIELD OF THE INVENTION

This invention relates to printed batteries and, in particular, to an array of printed batteries that can be interconnected by switches to provide a variable voltage and current to a load.

BACKGROUND

Printed batteries are well-known for use in low power applications. A typical voltage of a single printed battery is about 1-2 volts. To generate a higher voltage for a load, multiple batteries are printed, and traces permanently connect the batteries in series. DC/DC converters are also used to convert the voltage. To increase the maximum current supplied by a single printed battery, the battery is made larger.

When a battery is connected to the load, its useful lifetime is shortened.

In some cases, it may be desirable to power a load where the voltage or current requirements of the load may vary or where different loads may be connected to the same battery. Therefore, it is inefficient to use the conventional printed battery arrays with their fixed connections for such loads.

SUMMARY

In one embodiment, a plurality of battery cells is printed on a substrate, where each battery may output the same voltage, such as about 1.5 volts. Batteries in a first subset are connectable in parallel by controllable switches to control the maximum current that can be delivered to a load. Batteries in a second subset are also connectable in parallel by additional controllable switches to control the maximum current that can be delivered to the load. Another group of switches can either connect the two subsets of batteries in series, to generate 3 volts, or connect the subsets in parallel to increase the maximum current.

Additional subsets of batteries and their associated switches may be further connected to increase the voltage and current.

The switches may be printed field effect transistors (enhancement mode, or depletion mode, or a combination) or other suitable controllable switches.

A controller, also on the substrate, controls the switches (e.g., supplies a gate voltage to MOSFETs) to cause the array of batteries to supply the desired voltage and current to the load. A visual voltage indicator on the substrate may also be provided, such as an LED indicator, to give feedback to the user.

The load may also be printed on the substrate, or the load may be a pre-formed device (e.g., a medical sensor) that is attached to the power supply leads on the substrate. The load may have variable requirements for voltage and current, and the controller may dynamically control the switches based on such load requirements to most efficiently use the batteries. For example, it may be more efficient to electrically isolate batteries, when not needed, to maximize the overall lifetime of the power supply. Further, dead batteries may be electrically isolated from the load, and fresh batteries may be automatically connected to the load. The switches may be controlled to periodically vary which batteries supply power to the load to maximize the overall life of the power supply.

In another embodiment, to preserve battery life, the individual batteries may be selectively activated at any time for initiating the batteries' internal chemical reactions.

In one embodiment, the battery array, switches, and controller on a single substrate are standardized to form a variable power source, and the load is separately provided. A wide variety of loads may be powered by the power source, since the voltage and current provided can be customized by the user for the particular load. The load may or may not be mounted on the substrate.

The invention is particularly useful for applications where the substrate must be flexible and the battery life must be prolonged, such as for disposable skin patches for medical tests, product packaging, etc.

Other embodiments are disclosed.

DETAILED DESCRIPTION

Figure 1:
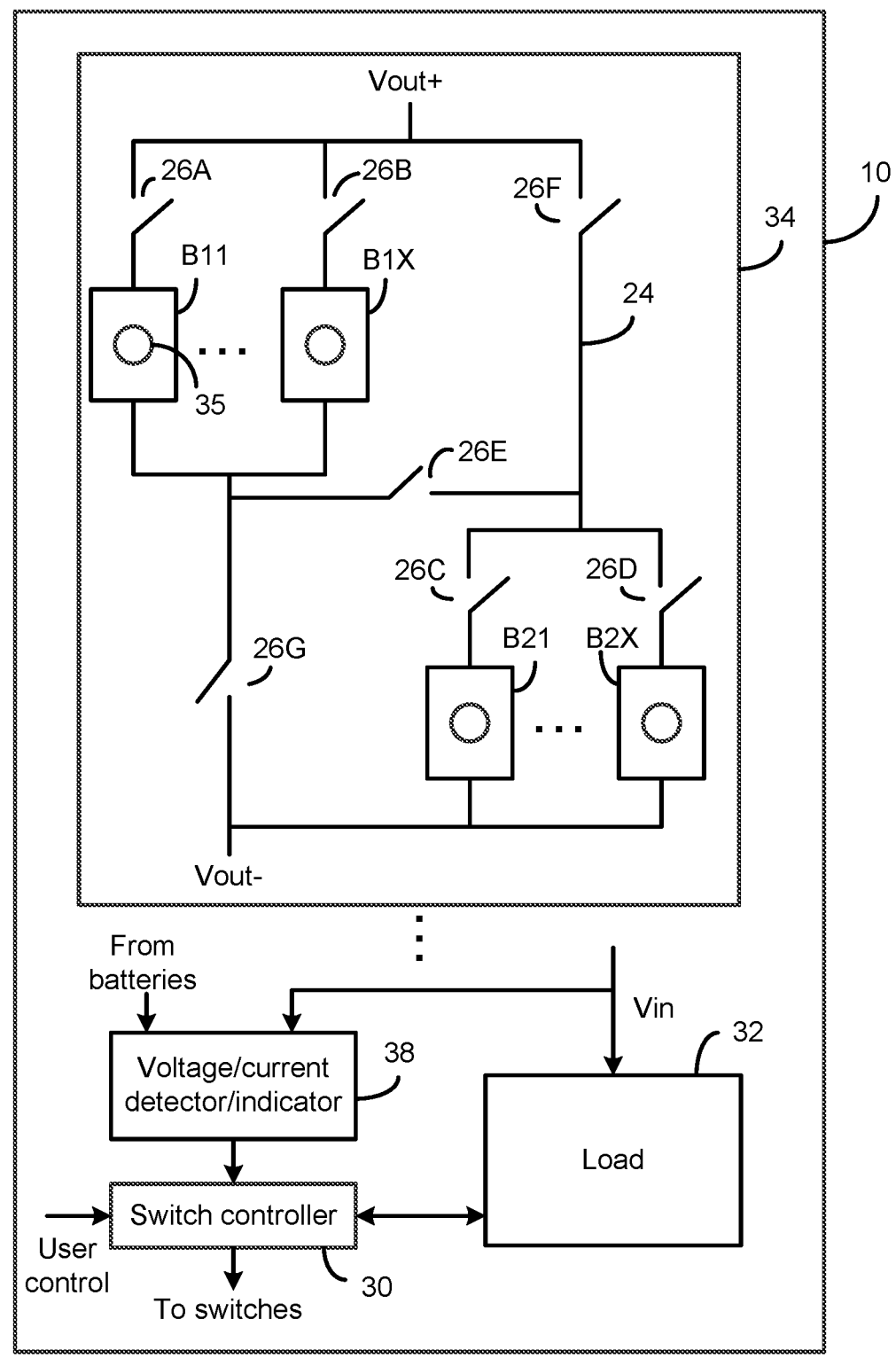
FIG. 1 is a schematic diagram of a flexible substrate having printed on it an array of interconnectable batteries for powering any type of load mounted on the substrate.

FIG. 1 illustrates a flexible substrate 10, such as a PMMA film, a PET film, any plastic film, cloth, paper, a metal film, or other suitable material.

Small batteries B11-B1X and B2-B2X are printed on the substrate 10. Such printed batteries may be silver-oxide batteries disclosed in US 2015/0024247, assigned to the present assignee and incorporated herein by reference, which generate electricity by chemical reactions within the battery. There are many well-known types of printed batteries that may be used instead. Any number of batteries may be located between batteries B11 and B1X and between B21 and B2X.

Figure 2:
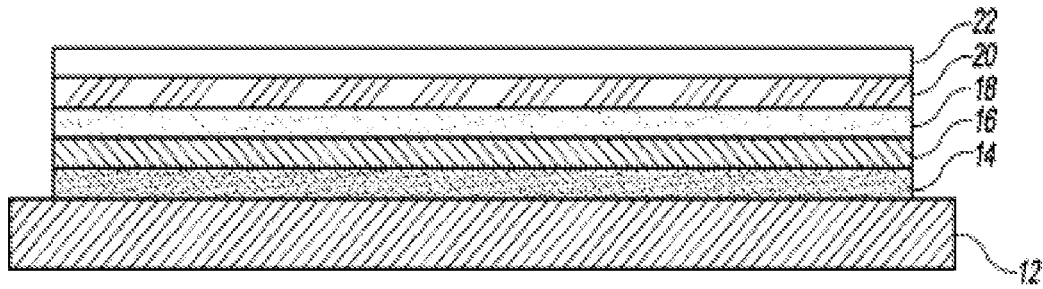
FIG. 2 is a cross-section of a printed battery from publication US 2015/0024247.

FIG. 2 is a cross-section of a battery taken from US 2015/0024247 and illustrates a substrate 12 (which may be the substrate 10 in FIG. 1), a first metal current collector layer 14 (a metal foil), a first active electrode layer 16, a separator layer 18, a second active electrode layer 20, and a second metal current collector layer 22 (a metal foil). The metal layers 14 and 22 are the anode and cathode conductors for the battery that are contacted by the printed metal traces 24 in FIG. 1. Electrical contact to the second metal current collector 22 by a trace 24 may be made by forming the second metal current collector 22 so that an end resides on the surface of the substrate 10 (FIG. 1) planar with the first metal current collector 14. This configuration makes it easier for the traces 24 to electrically contact the current collectors 14/22.

The electrodes 16/20 comprise gel or paste electrolytes that can be decomposed to supply ions for generating a voltage and providing current, as described in US 2015/

0024247. The cathode electrode additionally contains silver-oxide. The battery is referred to as a silver-oxide battery. The separator 18 is permeable to the ions produced and may be a polymer film, cellulose, or other suitable material. Such batteries generate between 1.1-1.8 volts, and the voltage drops as the battery become depleted. For example, the voltage may drop by half over a 24 hour period, depending on the current supplied by the battery, such as 100 uA. Many other well-known battery types can be printed such as lithium-ion batteries and NiCad batteries. The batteries may be rechargeable or non-rechargeable. The thickness of a printed battery is typically less than 1 mm.

In FIG. 1, each battery has a size that is suitable for the particular application. If the device is only for use for a short period (e.g., a few days), the batteries may be small, such as about 1 cm per side. For higher current needs or for more prolonged use needs, the batteries are made larger, such as 2 cm per side. The shapes of the batteries do not need to be squares, and different shapes, such as serpentine shapes, may provide known benefits.

The batteries described herein may be "single layer" types, as shown in FIG. 2, where there is only a single interface between two active electrodes, or multiple battery layers may be stacked over each other and interconnected in parallel or series to increase current or voltage. Stacked battery layers make more efficient use of the substrate surface area and may reduce resistive losses.

Controllable switches 26A-26G may also be printed on the substrate 10. Such switches may be FETs of the types used in active displays, such as described in US 2015/0280006, incorporated herein by reference. Such printed transistors are well-known. Many other types of printed switches can also be used. The switches are controlled by supplying a threshold signal to their gates or other control terminals.

The switches 26A and 26B connect the batteries B11 and B1X to the Vout+ terminal of the power supply. Identical switches are connected to other batteries located between the batteries B11 and B1X. The switches 26A and 26B are controlled by the controller 30 to connect any of the batteries B11-B1X to the load 32. In other words, such switches selectively connect the batteries B11-B1X in parallel. The batteries B11-B1X are in a first subset of the batteries. The load 32, such as medical diagnosis sensor adjacent a patient's skin, may also be printed on the substrate 10, or the load 32 may be pre-formed and mounted on the substrate 10 to electrically connect it to the power supply output terminals. If the device is a sensor for being attached to a patient's skin, the flexible substrate 10 is provided with an adhesive layer on its back surface. The load 32 may include memory for retaining sensor data for later downloading via an external computer. In one embodiment, the load is removable from the substrate 10 and reusable on another power supply substrate 10.

Similarly, the switches 26C and 26D, connecting the batteries B21 and B2X to the Vout– terminal of the power supply, and any switches connected to other batteries located between batteries B21 and B2X, are controlled by the controller 30 to connect any of the batteries B21-B1X to the load 32. In other words, such switches selectively connect the batteries B21-B2X in parallel. The batteries B21-B2X are in a second subset of the batteries.

The switches 26E-26G, also controlled by the controller 30, are used to connect the two subsets of batteries in series or in parallel. For a series connection, switches 26F and 26G are open and switch 26E is closed. The series connection sums the voltages from the first and second subsets of batteries. For a parallel connection, switches 26F and 26G are closed and switch 26E is open. The parallel connection sums the currents from the first and second subsets of batteries.

The power supply 34 may be replicated any number of times on the substrate to add more groups of batteries for selective connection in series or parallel with the power supply 34. All the switches are controlled by the controller 30.

The resulting battery voltage is applied across the load as the input voltage Vin.

The controller 30 may be a state machine or other inexpensive logic circuit that detects a power supply requirement of the load 32 and controls the switches 26A-26G to meet the power supply requirements of the load 32. For example, the load 32 may have an active mode and a sleep mode. During the active mode of the load 32, the controller 30 senses a signal from the load 32 and determines, based on a stored program or look-up table in the controller 30, which switches should be turned on or off to meet the higher current demand of the load 32. During a sleep mode (or off state) of the load 32, the controller 30 senses a signal from the load 32 and turns off some or all of the switches 26A-26G to disconnect batteries from the load to reduce drain on the batteries. Although an ideal battery has infinite resistance, actual batteries have a resistance, and removing unneeded batteries from the load 32 improves efficiency and increases the lifetime of the power supply.

A voltage/current indicator 38 may also be printed on the substrate 10 or mounted on the substrate 10. The voltage/current indicator 38 may detect the voltage of each battery and also detect the overall voltage Vin into the load 32. This may provide a feedback signal to the controller 30 to remove dead or unnecessary batteries from the load or to add more batteries in parallel or series to suitable change the voltage Vin or available current.

In another embodiment, the voltage/current indicator 38 includes printed light emitting diodes (LEDs) so that a user can readily determine the input voltage Vin into the load 32 to determine if it is the proper voltage. The LED display may also indicate which batteries are dead.

Instead of the controller 30 being totally automatically controlled, or in addition to the controller 30 being automatically controlled, the controller 30 may be manually controlled by the user via an external signal, small slide switches on the substrate 10, or push-button switches on the substrate 10 to cause the power supply to generate a desired voltage or current. The external signals may be digital or an analog voltage level to cause the controller 30 to supply the necessary control signals to the switches 26A-26G to generate the desired voltage or current. In one embodiment, each switch 26A-26G is directly user-controlled, such as by applying digital input signals to the controller 30, to allow the user to set the voltage Vin and current into the load 32.

If the voltage goes down over time, the controller 30 can be manually controlled or controlled automatically to increase the voltage to within a desired range.

Any integrated circuits or other electronic components may be mounted on the substrate 10 to perform a required function, such as to provide DC/DC voltage regulation, provide analog-to-digital conversion, measuring voltages and currents, or provide the load 32 function.

In one embodiment, in order to maximize the life of the power supply 34, different combinations of the batteries may be intermittently connected to the load 32 via the switches 26A-26G so that all the batteries become drained at about the same rate.

In one embodiment, all batteries are isolated from one another in a storage mode by all the switches 26A-26G being normally open. The user may then cause the device to be active just prior to use by, for example, manually turning on the controller 30 with a slide switch or push button switch. The batteries may power the controller 30, or the controller 30 may use a separate power source such as a coin-type battery.

In one embodiment, the controller 30 may temporarily increase the output voltage of the power supply 34 beyond a threshold to temporarily turn on a device, such as LEDs printed on the substrate 10, as an indicator or for another function, and then reduce the output voltage to an operating level.

In one embodiment, each battery may be inactive until the user activates the battery by starting the chemical reaction in the batteries. This is particularly useful when the device is to be stored for long periods of time. In one such embodiment, an insulating plastic tape may be initially inserted between the active layers of the battery so no chemical reactions occur. When the device is to be used, the tape is pulled out of the batteries to start the chemical reactions. Other techniques for activating a battery may entail pressing on a battery to break a seal, puncturing a seal in the battery, or tearing a seal. A seal to be broken is represented by a circle 35 within each battery. Prior to the battery being activated, it has a very high resistance so does not load down the circuit.

After the device is used for its intended purpose, the device may be disposed of, assuming the batteries are not rechargeable. The device may be inexpensive since most or all of the circuitry can be printed and any ICs or sensors should be inexpensive.

In one embodiment, the power supply 34 and circuitry on the substrate 10, other than the load 32, form a standardized variable power supply for a load. Various types of loads, such as medical sensors, etc., may be mounted to the standardized substrate 10 and connected to the power supply 34 terminals and to the controller 30 via traces 24. The load does not have to be mounted to the substrate 10. The loads may have different power requirements, and the controller 30 controls the switches to supply the required voltage and current to the particular load. For example, a load may provide a signature resistance or other characteristic to the controller 30 signifying its power requirements, and the controller then determines the most efficient interconnections of the batteries needed to meet the load's power requirements. Alternatively, the user controls the controller 30 to switch any combination of the switches, and the controller 30 supplies the required signals to the switches (e.g., gate voltages) to close them.

Figure 3:
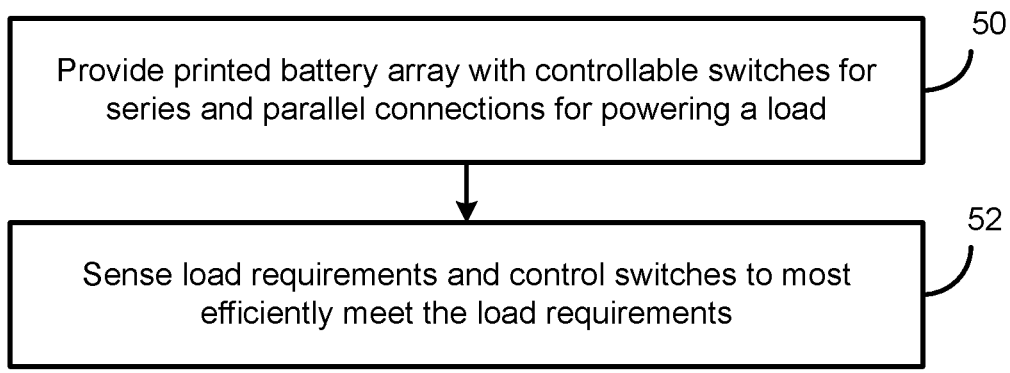
FIG. 3 is a flowchart identifying steps performed by the battery power supply of FIG. 1.

FIG. 3 is a flowchart identifying various steps employed by the device of FIG. 1. In step 50, the printed batteries, traces, switches, and other circuitry are provided on the substrate 10. In step 52, the load requirements are sensed and the controller closes or opens the switches 26A-26G to most efficiently supply the required voltage and current to the load.

Alternatively, the user controls the switches to supply the required voltage and current to the load.

Figure 4:
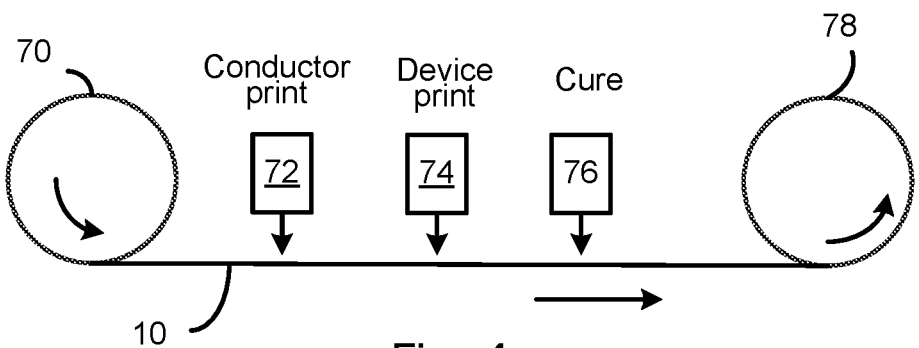
FIG. 4 illustrates a roll-to-roll process for inexpensively printing components on a flexible substrate.

FIG. 4 illustrates a roll-to-roll process for fabricating the device. The flexible substrate 10 is provided on a first roll 70. The substrate 10 processing may be standardized and any customized loads or other circuits are mounted later on the standardized power supply substrate 10. This greatly reduces the overall cost of the device. The substrate 10 acts as a flexible circuit. At station 72, the conductive traces or other conductor layers are printed by depositing a metal ink and curing the ink. In step 74, the batteries, switches, and any other suitable components are printed on the substrate 10. In step 76, the various inks are cured. The resulting substrate 10 is taken up by a take up roll 78 or singulated as sheets.

Other devices may be printed on the substrate 10, such as photovoltaic devices, etc.

While particular embodiments of the present invention have been shown and described, it will be obvious to those skilled in the art that changes and modifications may be made without departing from this invention in its broader aspects and, therefore, the appended claims are to encompass within their scope all such changes and modifications as fall within the true spirit and scope of this invention.

What is claimed is:

1. A powered device comprising:
   a substrate;
   a power supply on the substrate comprising:
      a positive output terminal and a negative output terminal;
      a plurality of printed batteries on the substrate, the plurality of batteries comprising first batteries in a first subset of batteries and second batteries in a second subset of batteries;
      a plurality of switches connected to the plurality of batteries, the switches comprising first switches that selectively connect the first batteries in the first subset of batteries in parallel, second switches that selectively connect the second batteries in the second subset of batteries in parallel, third switches that selectively connect the first subset of batteries in series with the second subset of batteries, and fourth switches that selectively connect the first subset of batteries in parallel with the second subset of batteries; and
   a controller on the substrate controlling the first switches, the second switches, the third switches, and the fourth switches.

2. The device of claim 1 wherein the controller automatically controls the plurality of switches.

3. The device of claim 2 wherein the controller automatically controls the plurality of switches based on feedback signals from the batteries.

4. The device of claim 2 further comprising a load coupled to the positive output terminal and the negative output terminal, wherein the controller automatically controls the plurality of switches based on signals from the load.

5. The device of claim 1 wherein the controller is controlled by a user to control the plurality of switches.

6. The device of claim 1 wherein the switches are printed transistors.

7. The device of claim 1 further comprising a voltage detector on the substrate that indicates an output voltage of the power supply.

8. The device of claim 1 further comprising a voltage detector on the substrate that indicates an output voltage of each of the batteries.

9. The device of claim 1 further comprising a voltage detector on the substrate that provides a feedback signal to the controller for controlling the plurality of switches.

10. The device of claim 9 wherein the controller automatically reconfigures the switches to cause the power supply to output a particular voltage.

11. The device of claim 1 wherein the controller is configured to maintain all the switches in an open state until the device is to be used.

12. The device of claim 1 wherein all the switches are normally opened until closed by the controller.

13. The device of claim 1 wherein the controller is configured for electrically isolating a battery via one or more of the switches when the controller determines that the battery has sufficiently lost its charge.

14. The device of claim 1 further comprising a load coupled to the positive output terminal and the negative output terminal, wherein the controller periodically connects some batteries to the load and disconnects other batteries from the load to prolong an effective life of the power supply.

15. The device of claim 1 further comprising a load coupled to the positive output terminal and the negative output terminal, wherein the substrate is flexible and the load is a sensor.

16. The device of claim 15 further comprising a load coupled to the positive output terminal and the negative output terminal, wherein the load is a medical sensor for a patient, the device further comprising an adhesive layer on a surface of the substrate for attaching to the patient's skin for placing the load proximate to the patient's skin.

17. The device of claim 15 further comprising a load supported by the substrate and coupled to the positive output terminal and the negative output terminal.

18. A method of supplying power to a load comprising:
providing a variable power supply on a substrate, the power supply comprising:
a positive output terminal and a negative output terminal;
a plurality of printed batteries on the substrate, the plurality of batteries comprising first batteries in a first subset of batteries and second batteries in a second subset of batteries;
a plurality of switches connected to the plurality of batteries, the switches comprising first switches that selectively connect the first batteries in the first subset of batteries in parallel, second switches that selectively connect the second batteries in the second subset of batteries in parallel, third switches that selectively connect the first subset of batteries in series with the second subset of batteries, and fourth switches that selectively connect the first subset of batteries in parallel with the second subset of batteries; and
a controller on the substrate controlling the first switches, the second switches, the third switches, and the fourth switches;
connecting a load to the positive output terminal and the negative output terminal, the load having electrical input requirements; and
supplying signals by the controller to close selected ones of the plurality of switches to output a voltage across the positive output terminal and the negative output terminal to meet the electrical input requirements of the load.

19. The method of claim 18 wherein the controller automatically detects the electrical requirements of the load and automatically supplies the signals to close the selected ones of the plurality of switches to output the voltage across the positive output terminal and the negative output terminal to meet the electrical input requirements of the load.

20. The method of claim 18 wherein the controller is controlled by a user to supply the signals to close the selected ones of the plurality of switches to output the voltage across the positive output terminal and the negative output terminal to meet the electrical input requirements of the load.

* * * * *